US006398752B1

(12) United States Patent
Sweezer, Jr. et al.

(10) Patent No.: US 6,398,752 B1
(45) Date of Patent: *Jun. 4, 2002

(54) METHOD OF OCCLUDING A PATIENT'S ASCENDING AORTA AND DELIVERY CARDIOPLEGIC FLUID

(76) Inventors: William P. Sweezer, Jr., 3443 Stage Coach Dr., Lafayette, CA (US) 94549; Ronald Coleman, 2831 61st Ave., Oakland, CA (US) 94605; Walter W. Larkins, III, 1988 Rolling Vista Dr., #20, Lomita, CA (US) 90717

( * ) Notice: Subject to any disclaimer, the term of this patent is extended or adjusted under 35 U.S.C. 154(b) by 0 days.

This patent is subject to a terminal disclaimer.

(21) Appl. No.: 09/092,374

(22) Filed: Jun. 5, 1998

Related U.S. Application Data

(63) Continuation of application No. 08/566,405, filed on Dec. 1, 1995, now Pat. No. 5,765,568, which is a continuation-in-part of application No. 08/250,721, filed on May 27, 1994, now Pat. No. 5,478,309.

(51) Int. Cl.[7] .............................................. A61M 37/00
(52) U.S. Cl. ...................... 604/6.14; 604/4.01; 128/898
(58) Field of Search .................... 128/898; 604/96–102, 604/4–6, 49, 95, 27, 53, 401, 6.06, 6.11, 6.14, 6.16

(56) References Cited

U.S. PATENT DOCUMENTS

| 150,960 A | 5/1874 | Isbell |
| 231,601 A | 8/1880 | Meigs |
| 280,225 A | 6/1883 | Noe |
| 299,622 A | 6/1884 | Chase |
| 303,757 A | 8/1884 | Sears et al. |
| 1,282,881 A | 10/1918 | Landis |
| 2,029,236 A | 1/1936 | Klophaus |
| 2,308,484 A | 1/1943 | Auzin et al. |

(List continued on next page.)

FOREIGN PATENT DOCUMENTS

| DE | 2246526 B2 | 3/1973 |
| EP | 0103546 A1 | 3/1984 |
| EP | 0 335 205 | 1/1985 |
| EP | 0 161 045 | 11/1985 |
| EP | 0218275 A1 | 4/1987 |
| EP | 0 218 275 | 4/1987 |

(List continued on next page.)

OTHER PUBLICATIONS

Andersen et al., "Transluminal Implantation of Artificial Heart Valves," *European Heart Journal*, 1992; 13:704–708.
Buckberg, G.D., "Strategies and Logic of Cardioplegic Delivery to Prevent, Avoid, and Reverse Ischemic and Reperfusion Damage," *J Thorac Cardio Vasc Surg*, 1987; 93:127–129.

(List continued on next page.)

*Primary Examiner*—Glenn K. Dawson
*Assistant Examiner*—Jennifer Maynard

(57) ABSTRACT

An extracorporeal support system including an extracorporeal support apparatus and an arterial circulation support catheter. The arterial circulation support catheter includes a blood lumen with a proximal end coupled to extracoporeal support apparatus and a distal end inserted into the blood circulation. A vent lumen has a distal end that crosses the aortic valve into the left ventricle and provides direct venting of the left ventricle through the vent lumen. An arterial circulation support catheter occluding member is positioned either in an interior or at an exterior of the arterial circulation support catheter. A venous circulation support catheter is provided and includes a blood lumen with a proximal end coupled to the extracorporeal support apparatus and a distal end inserted into the blood circulation. A venous circulation support catheter occluding member is included and positioned in an interior or at an exterior of the venous circulation support catheter. The venous circulation support catheter occluding member occludes the superior vena cava and the inferior vena cave

4 Claims, 10 Drawing Sheets

U.S. PATENT DOCUMENTS

| | | |
|---|---|---|
| 2,531,730 A | 11/1950 | Henderson |
| 2,854,982 A | 10/1958 | Pagano |
| 3,326,648 A | 6/1967 | Provisor |
| 3,385,300 A | 5/1968 | Holter |
| 3,409,013 A | 11/1968 | Berry |
| 3,547,119 A | 12/1970 | Hall |
| 3,587,115 A | 6/1971 | Shiley |
| 3,635,223 A | 1/1972 | Klieman |
| 3,671,979 A | 6/1972 | Moulopoulos |
| 3,674,014 A | 7/1972 | Tillander |
| 3,692,018 A | 9/1972 | Goetz et al. |
| 3,755,823 A | 9/1973 | Hancock |
| 3,766,924 A | 10/1973 | Pidgeon |
| 3,769,960 A | 11/1973 | Robinson |
| 3,788,328 A | 1/1974 | Alley et al. |
| 3,833,003 A | 9/1974 | Taricco |
| 3,837,347 A | 9/1974 | Tower |
| 3,851,647 A | 12/1974 | Monestere, Jr. et al. |
| 3,889,686 A | 6/1975 | Duturbure |
| 3,903,895 A | 9/1975 | Alley et al. |
| 3,915,171 A | 10/1975 | Shermeta |
| 3,963,028 A | 6/1976 | Cooley et al. |
| 3,970,090 A | 7/1976 | Loiacono |
| 3,983,879 A | 10/1976 | Todd |
| 4,000,739 A | 1/1977 | Stevens |
| 4,019,515 A | 4/1977 | Kornblum et al. |
| 4,029,104 A | 6/1977 | Kerber |
| 4,038,703 A | 8/1977 | Bokros |
| 4,056,854 A | 11/1977 | Boretos et al. |
| 4,073,297 A | 2/1978 | Kopp |
| 4,106,129 A | 8/1978 | Carpentier et al. |
| 4,122,858 A | 10/1978 | Schiff |
| 4,154,227 A | 5/1979 | Krause et al. |
| 4,173,981 A | 11/1979 | Mortensen |
| 4,204,328 A | 5/1980 | Kutner |
| 4,222,126 A | 9/1980 | Boretos et al. |
| 4,248,224 A | 2/1981 | Jones |
| 4,276,874 A | 7/1981 | Wolvek et al. |
| 4,284,073 A | 8/1981 | Krause et al. |
| 4,285,341 A | 8/1981 | Pollack |
| 4,287,892 A | 9/1981 | Schiff |
| 4,289,129 A | 9/1981 | Turner |
| 4,290,428 A | 9/1981 | Durand et al. |
| 4,297,749 A | 11/1981 | Davis et al. |
| 4,301,803 A | 11/1981 | Handa et al. |
| 4,304,239 A | 12/1981 | Perlin |
| 4,310,017 A | 1/1982 | Raines |
| 4,323,071 A | 4/1982 | Simpson et al. |
| 4,327,709 A | 5/1982 | Hanson et al. |
| 4,328,056 A | 5/1982 | Snooks |
| 4,343,048 A | 8/1982 | Ross et al. |
| 4,351,341 A | 9/1982 | Goldberg et al. |
| 4,405,313 A | 9/1983 | Sisley et al. |
| 4,411,055 A | 10/1983 | Simpson et al. |
| 4,413,989 A | 11/1983 | Schjeldahl et al. |
| 4,417,576 A | 11/1983 | Baran |
| 4,430,081 A | 2/1984 | Timmermans |
| 4,439,186 A | 3/1984 | Kuhl |
| 4,441,495 A | 4/1984 | Hicswa |
| 4,451,251 A | 5/1984 | Osterholm |
| 4,456,000 A | 6/1984 | Schjeldahl et al. |
| 4,459,977 A | 7/1984 | Pizon |
| 4,464,175 A | 8/1984 | Altman et al. |
| 4,493,697 A | 1/1985 | Krause et al. |
| 4,496,345 A | 1/1985 | Hasson |
| 4,497,325 A | 2/1985 | Wedel |
| 4,512,762 A | 4/1985 | Spears |
| 4,527,549 A | 7/1985 | Gabbay |
| 4,531,935 A | 7/1985 | Berryessa |
| 4,531,936 A | 7/1985 | Gordon |
| 4,535,757 A | 8/1985 | Webster, Jr. |
| 4,540,399 A | 9/1985 | Litzie et al. |
| 4,552,558 A | 11/1985 | Muto |
| 4,573,966 A | 3/1986 | Weikl et al. |
| 4,574,803 A | 3/1986 | Storz |
| 4,580,568 A | 4/1986 | Gianturco |
| 4,592,340 A | 6/1986 | Boyles |
| 4,596,552 A | 6/1986 | DeVries |
| 4,601,706 A | 7/1986 | Aillon |
| 4,601,713 A | 7/1986 | Fuqua |
| 4,610,661 A | 9/1986 | Possis et al. |
| 4,612,011 A | 9/1986 | Kautzky |
| 4,631,052 A | 12/1986 | Kensey |
| 4,639,252 A | 1/1987 | Kelly et al. |
| 4,648,384 A | 3/1987 | Schmukler |
| 4,664,125 A | 5/1987 | Pinto |
| 4,681,117 A | 7/1987 | Brodman et al. |
| 4,686,085 A | 8/1987 | Osterholm |
| 4,689,041 A | 8/1987 | Corday et al. |
| 4,692,148 A | 9/1987 | Kantrowitz et al. |
| 4,697,574 A | 10/1987 | Karcher et al. |
| 4,704,102 A | 11/1987 | Guthery |
| 4,705,507 A | 11/1987 | Boyles |
| 4,714,460 A | 12/1987 | Calderon |
| 4,721,109 A | 1/1988 | Healey |
| 4,722,347 A | 2/1988 | Abrams et al. |
| 4,722,732 A | 2/1988 | Martin |
| 4,723,550 A | 2/1988 | Bales et al. |
| 4,723,936 A | 2/1988 | Buchbinder et al. |
| 4,733,665 A | 3/1988 | Palmaz |
| 4,741,328 A | 5/1988 | Gabbay |
| 4,751,924 A | 6/1988 | Hammerschmidt et al. |
| 4,753,637 A | 6/1988 | Horneffer |
| 4,767,409 A | 8/1988 | Brooks |
| 4,770,652 A | 9/1988 | Mahurkar |
| 4,771,777 A | 9/1988 | Horzewski et al. |
| 4,777,951 A | 10/1988 | Cribier et al. |
| 4,785,795 A | 11/1988 | Singh |
| 4,787,899 A | 11/1988 | Lazarus |
| 4,787,901 A | 11/1988 | Baykut |
| 4,790,825 A | 12/1988 | Bernstein et al. |
| 4,794,928 A | 1/1989 | Kletschka |
| 4,796,629 A | 1/1989 | Grayzel |
| 4,798,588 A | 1/1989 | Aillon |
| 4,804,358 A | 2/1989 | Karcher et al. |
| 4,804,365 A | 2/1989 | Litzie et al. |
| 4,808,165 A | 2/1989 | Carr |
| 4,809,681 A | 3/1989 | Kantrowitz et al. |
| 4,811,737 A | 3/1989 | Rydell |
| 4,821,722 A | 4/1989 | Miller et al. |
| 4,830,849 A | 5/1989 | Osterholm |
| 4,848,344 A | 7/1989 | Sos et al. |
| 4,850,969 A | 7/1989 | Jackson |
| 4,856,516 A | 8/1989 | Hillstead |
| 4,865,581 A | 9/1989 | Lundquist et al. |
| 4,877,031 A | 10/1989 | Conway et al. |
| 4,877,035 A | 10/1989 | Bogen et al. |
| 4,878,495 A | 11/1989 | Grayzel |
| 4,883,458 A | 11/1989 | Shiber |
| 4,886,507 A | 12/1989 | Patton et al. |
| 4,889,137 A | 12/1989 | Kolobow |
| 4,898,168 A | 2/1990 | Yule |
| 4,902,272 A | 2/1990 | Milder et al. |
| 4,902,273 A | 2/1990 | Choy et al. |
| 4,917,667 A | 4/1990 | Jackson |
| 4,923,450 A | 5/1990 | Maeda et al. |
| 4,927,412 A | 5/1990 | Menasche |
| 4,934,996 A | 6/1990 | Mohl et al. |
| RE33,258 E | 7/1990 | Onik et al. |

| | | |
|---|---|---|
| 4,943,275 A | 7/1990 | Stricker |
| 4,943,277 A | 7/1990 | Bolling |
| 4,960,412 A | 10/1990 | Fink |
| 4,966,604 A | 10/1990 | Reiss |
| 4,969,470 A | 11/1990 | Mohl et al. |
| 4,979,939 A | 12/1990 | Shiber |
| 4,985,014 A | 1/1991 | Orejola |
| 4,986,830 A | 1/1991 | Owens et al. |
| 4,990,143 A | 2/1991 | Sheridan |
| 4,994,032 A | 2/1991 | Sugiyama et al. |
| 4,994,033 A | 2/1991 | Shockey et al. |
| 5,007,896 A | 4/1991 | Shiber |
| 5,009,636 A | 4/1991 | Wortley et al. |
| 5,011,468 A | 4/1991 | Lundquist et al. |
| 5,011,469 A | 4/1991 | Buckberg et al. |
| 5,011,488 A | 4/1991 | Ginsburg |
| 5,013,296 A | 5/1991 | Buckberg et al. |
| 5,021,044 A | 6/1991 | Sharkaway |
| 5,021,045 A | 6/1991 | Buckberg et al. |
| 5,024,668 A | 6/1991 | Peters et al. |
| 5,026,366 A | 6/1991 | Leckrone |
| 5,032,128 A | 7/1991 | Alonso |
| 5,033,998 A | 7/1991 | Corday et al. |
| 5,037,434 A | 8/1991 | Lane |
| 5,041,093 A | 8/1991 | Chu |
| 5,041,098 A | 8/1991 | Loiterman et al. |
| 5,047,041 A | 9/1991 | Samuels |
| 5,049,132 A | 9/1991 | Shaffer et al. |
| 5,053,008 A | 10/1991 | Bajaj |
| 5,059,167 A | 10/1991 | Lunquist et al. |
| 5,069,661 A | 12/1991 | Trudell |
| 5,069,662 A | 12/1991 | Bodden |
| 5,073,168 A | 12/1991 | Danforth |
| 5,080,660 A | 1/1992 | Buelna |
| 5,088,984 A | 2/1992 | Fields |
| 5,089,015 A | 2/1992 | Ross |
| 5,106,368 A | 4/1992 | Uldall et al. |
| 5,109,859 A | 5/1992 | Jenkins |
| 5,112,305 A | 5/1992 | Barath et al. |
| 5,116,305 A | 5/1992 | Milder et al. |
| 5,125,903 A | 6/1992 | McLaughlin et al. |
| 5,152,771 A | 10/1992 | Sabbaghian et al. |
| 5,163,953 A | 11/1992 | Vince |
| 5,167,628 A | 12/1992 | Boyles |
| 5,171,232 A | 12/1992 | Castillo et al. |
| 5,176,619 A | 1/1993 | Segalowitz |
| 5,181,518 A | 1/1993 | McDonagh et al. |
| 5,186,713 A | 2/1993 | Raible |
| 5,195,942 A | 3/1993 | Weil et al. |
| 5,197,952 A | 3/1993 | Marcadis et al. |
| 5,216,032 A | 6/1993 | Manning |
| 5,219,326 A | 6/1993 | Hattler |
| 5,226,427 A | 7/1993 | Buckberg et al. |
| 5,236,413 A | 8/1993 | Feiring |
| 5,246,007 A | 9/1993 | Frisbie et al. |
| 5,250,038 A | 10/1993 | Melker et al. |
| 5,250,069 A | 10/1993 | Nobuyoshi et al. |
| 5,254,089 A | 10/1993 | Wang |
| 5,254,097 A | 10/1993 | Shock et al. |
| 5,270,005 A | 12/1993 | Raible |
| 5,275,622 A | 1/1994 | Lazarus et al. |
| 5,290,231 A | 3/1994 | Marcadis et al. |
| 5,295,958 A | 3/1994 | Shturman |
| 5,308,320 A | 5/1994 | Safar et al. |
| 5,312,344 A | 5/1994 | Grinfield et al. |
| 5,314,418 A | 5/1994 | Takano et al. |
| 5,322,500 A | 6/1994 | Johnson et al. |
| 5,322,509 A | 6/1994 | Rickerd |
| 5,324,260 A | 6/1994 | O'Neill et al. |
| 5,330,451 A | 7/1994 | Gabbay |
| 5,332,402 A | 7/1994 | Teitelbaum |

| | | |
|---|---|---|
| 5,334,142 A | 8/1994 | Paradis |
| 5,370,618 A | 12/1994 | Leonhardt |
| 5,370,640 A | 12/1994 | Kolff |
| 5,370,685 A | 12/1994 | Stevens |
| 5,374,245 A | 12/1994 | Mahurkar |
| 5,380,282 A | 1/1995 | Burns |
| 5,382,239 A | 1/1995 | Orr et al. |
| 5,383,854 A | 1/1995 | Safar et al. |
| 5,385,548 A | 1/1995 | Williams et al. |
| 5,395,330 A | 3/1995 | Marcadis et al. |
| 5,395,331 A | 3/1995 | O'Neill et al. |
| 5,397,306 A | 3/1995 | Nobuyoshi et al. |
| 5,397,351 A | 3/1995 | Pavcnik et al. |
| 5,411,027 A | 5/1995 | Wiklund et al. |
| 5,411,479 A | 5/1995 | Bodden |
| 5,411,552 A | 5/1995 | Andersen et al. |
| 5,421,825 A | 6/1995 | Farcot |
| 5,423,772 A | 6/1995 | Lurie et al. |
| 5,425,705 A | 6/1995 | Evard et al. |
| 5,425,708 A | 6/1995 | Nasu |
| 5,428,070 A | 6/1995 | Cooke et al. |
| 5,433,700 A | 7/1995 | Peters |
| 5,437,633 A | 8/1995 | Manning |
| 5,439,443 A | 8/1995 | Miyata et al. |
| 5,443,446 A | 8/1995 | Shturman |
| 5,451,207 A | 9/1995 | Yock |
| 5,452,733 A | 9/1995 | Sterman et al. |
| 5,456,665 A | 10/1995 | Postell et al. |
| 5,458,574 A | 10/1995 | Machold et al. |
| 5,478,309 A | 12/1995 | Sweezer et al. |
| 5,480,424 A | 1/1996 | Cox |
| 5,487,730 A | 1/1996 | Marcadis et al. |
| 5,488,960 A | 2/1996 | Toner |
| 5,499,996 A | 3/1996 | Hill |
| 5,501,698 A | 3/1996 | Roth et al. |
| 5,505,698 A | 4/1996 | Booth et al. |
| 5,509,897 A | 4/1996 | Twardowski et al. |
| 5,525,388 A | 6/1996 | Wand et al. |
| 5,527,292 A | 6/1996 | Adams et al. |
| 5,533,957 A | 7/1996 | Aldea |
| 5,536,251 A | 7/1996 | Evard et al. |
| 5,545,214 A | 8/1996 | Stevens |
| 5,549,581 A | 8/1996 | Lurie et al. |
| 5,558,644 A | 9/1996 | Boyd et al. |
| 5,562,606 A | 10/1996 | Huybregts |
| 5,571,215 A | 11/1996 | Sterman et al. |
| 5,578,010 A | 11/1996 | Ashby |
| 5,584,803 A | 12/1996 | Sweezer et al. |
| 5,591,129 A | 1/1997 | Shoup et al. |
| 5,595,181 A | 1/1997 | Hubbard |
| 5,597,377 A | 1/1997 | Aldea et al. |
| 5,599,305 A | 2/1997 | Hermann et al. |
| 5,599,329 A | 2/1997 | Gabbay |
| 5,759,170 A * | 6/1998 | Peters .......................... 604/4 |
| 5,814,016 A * | 9/1998 | Valley et al. .................. 604/96 |
| 5,868,703 A * | 2/1999 | Bertolero et al. ........... 604/102 |

FOREIGN PATENT DOCUMENTS

| | | |
|---|---|---|
| EP | 0218275 | 4/1987 |
| EP | 0 249 338 | 5/1987 |
| EP | 0 238 106 | 9/1987 |
| EP | 0 277 367 | 8/1988 |
| EP | 0 321 614 | 6/1989 |
| EP | 0350302 A1 | 7/1989 |
| EP | 0 350 302 | 7/1989 |
| EP | 0350302 | 7/1989 |
| EP | 0357003 A2 | 3/1990 |
| EP | 0414350 A1 | 6/1990 |
| EP | 0 414 350 | 6/1990 |
| EP | 0414350 A13 | 6/1990 |
| GB | 1097881 | 3/1965 |

| GB | 1097882 | 3/1965 |
| GB | 1284701 | 4/1971 |
| GB | 1467976 | 3/1974 |
| GB | 1477665 | 4/1974 |
| GB | 1513918 | 8/1975 |
| GB | 2056023 A | 3/1981 |
| IT | 334404 | 1/1936 |
| SU | 1271508 A1 | 11/1986 |
| SU | 1371701 A1 | 2/1988 |
| WO | WO 81/03613 | 12/1981 |
| WO | WO 83/03204 | 9/1983 |
| WO | WO 89/10155 | 11/1989 |
| WO | WO 9101689 | 2/1991 |
| WO | WO 9108791 | 6/1991 |
| WO | WO 91/10456 | 7/1991 |
| WO | WO 91/17720 | 11/1991 |
| WO | WO 9117720 | 11/1991 |
| WO | WO 92/17118 | 10/1992 |
| WO | WO 9217118 | 10/1992 |
| WO | WO 93/07927 | 10/1992 |
| WO | WO 95/30447 | 11/1995 |

OTHER PUBLICATIONS

Cosgrove, D.M., "Management of the Calcified Aorta: An Alternative Method of Occlusion," *Ann Thorac Surg*, 1983; 36:718–719.

Crooke et al., "Biventricular Distribution of Cold Blood Cardioplegic Solution Administered by different Retrograde Techniques," *J Cardiac Thorac Surg*, 1991;102(4):631–636.

Derwent Abstract No. 87–190867/27 (1987), SU 127508 (Gorki Kirov Medical Ins.).

Erath, H.G. Jr. & Stoney, W.S. Jr., "Balloon Catheter Occlusion of the Ascending Aorta," *Ann Thorac Surg*, 1983; 35:560–561.

Foster, J.H. & Threlkel, J.B., "Proximal Control of Aorta with a Balloon Catheter," *Surg, Gynecology & Obstetrics*, 1971; pp. 693–694.

Gundry, et al., "A Comparison of Retrograde Cardioplegia Versus Antegrade Cardioplegia in the Presence of Coronary Artery Obstruction," *Ann Thorac Surg*, 1984; 38(2):124–127.

Ishizaka, "Myocardial Prtotection by Retrograde Cardiac Perfusion with cold Medified Krebs Solution Through Coroanry Sinys During Complete Ischemic Arrest for 120 Minutes," *J Jpn Assn Thorac Surg*, 1977; 25(12):1592–1601.

Lust et al., "Improved Protection of Chronically Inflow–Limited Myocardium with Retrograde Coronary Sinus Cardioplegia," *Circulation III*, 1988; 78(5):217–223.

Occlusion Balloon Catheters: Instructions for Use, *MediTech, Boston Scientific Corporation*, Rev. 3/91.

"Valvular Heart Disease," Sixteenth Edition of *The Merck Manual of Diagnosis and Therapy*, 1992; pp. 546–553.

Ogawa, K., "Aortic Arch Reconstruction Without Aortic Cross–Clamping Using Separate Extracorporeal Circulation," *J Jpn Assn Thorac Surg*, 1993; pp. 2185–2190.

Okita et al., "Utilization of Triple–Lumen Balloon Catheter for Occlusion of the Ascending aorta During Distal Aortic Arch Surgery with Hypothermic Retrograde Cerebral Circulation Technique through Left Thoracotomy," *Journal of Cardiac Surgery*, 1996; 10:699–702.

Peters, W.S., "The Promise of Cardioscopic Surgery," *AustralAs J Cardiac Thorac Surg*, 1993; 2(3):152–154.

Razi, D.M. "The Challenge of Calcific Aortitits," *J Cardiac Thorac Surg*, 1993; 8:102–107.

Rossi, F., "Long–Term Cardiopulmonary Bypass by Peripheral Cannulation in a Model of Total Heart Failure," *J Thorac Cardiac Vasc Surg*, 1990; 100:914–921.

Sabiston, D.C., *Textbook of Surgery*, $10^{th}$ Ed. 1972; pp. 2021–2023, 2114–2121.

Sakaguchi et al., "Aortic Valve Replacement and Coronary Artery Bypass," *J Jpn Assn Thorac Surg*, 1993; 41(6):1063–1068.

Takahashi, M. "Retrograde Coronary Sinus Perfusion for Myocardial Protection in Aortic Valve Surgery," *J Jpn Assn Thorac Surg*, 1982; 30(3):306–318.

Uchida, et al., "Percutaneous Cardiomyotomy and Valvulotomy with Angioscopic Guidance," *American Heart Journal*, 1991; 121(4, part 1):1221–1224.

Uchida et al., "Percutaneous Fiberoptic Angioscopy of the Cardiac Valves," *American Heart Journal*, 1991; 121(6, part 1):1791–1798.

Yamaguchi, A., "A Case of Reoperation Using a Balloon Catheter with Blocked Pars Ascendes Aortae," *Kyobu Geka*, 1991; 42(11):961–964.

Andersen et al., "Transluminal Implantation of Artificial Heart Valves . . . " *European Heart Journal*, 1992;13:704–708.

Baxter Healthcare Corporation, "Fogarty Occlusion Catheter: Instructions for Use," ©1994.

Buckberg, G.D., "Strategies and Logic of Cardioplegic Delivery to Prevent, Avoid, and Reverse Ischemic and Reperfusion Damage," *J Thorac Vasc Surg*, 1987; 93:127–129.

Corday et al., "Symposium on the Present Status of Reperfusion of the Acutely Ischemic Myocardium. Part I," *J. Am Coll Cardiol*, 1983; 1(4):1031–1036.

Cosgrove, D.M. "Management of the Calcified Aorta: An Alternative Method of Occlusion," *Ann Thorac Surg*, 1983;36:718–719.

Crooke et al., "Biventricular Distribution of Cold Blood Cardioplegic Solution Administered by Different Retrograde Techniques," *J Cardiac Thorac Surg*, 1991;102(4):631–636.

Datascope FDA 510(k) Application, "Percluder–DL Occluding Balloon," Oct. 12, 1993.

DLP, Inc., Directions for Use: Cardioplegic Pressure Cannula with Vent Line, Code #14009 9 Gauge (no date).

DLP Medtronic Alternative Access Cannulae Brochure, ©1995.

DLP Worldwide Medical Innovations, Instrument Listings, pp. 5–9.

Douville et al., "Retrograde Versus Antegrade Cardioplegia: Impact on Right Ventricular Function," *Ann Thorac Surg*, 1992; 54:56–61.

Drinkwater et al., "The Use of Combined Antegrade–Retrograde Infusion of Blood Cardioplegic Solution in Pediatric Patients Undergoing Heart Operations," *Thorac and Cardiovascular Surg*, 1992; 104(5):1349–1355.

Elecath, "Bain Coronary Sinus Flow Catheter for Jugular Entry," Catalog No. 75–2337, 1994.

Erath and Stoney, "Balloon Catheter Occlusion of the Ascending Aorta," *Ann Thorac Surg*, 1983;35:560–561.

Farcot et al., "New Catheter–Pump System for Diastolic Synchronized Coronary Sinus Retroperfusion (D.S.R.)," *Med Prog Technol*, 1980; 8(1):29–37.

Farcot et al., "Synchronized Retroperfusion of Coronary Veins for Circulatory Support of Jeopardized Ischemic Myocardium," *Am J Cardiol*, 1978; 41:1101–1201.

Foster and Threlkel, "Proximal Control of Aorta with a Balloon Catheter," *Surg Gynecology & Obstetrics*, 1971, pp. 693–694.

Gundry et al., "A Comparison of Retrograde of Cardioplegia Versus Antegrade Cardioplegia in the Presence of Coronary Artery Obstruction," Ann Thorac Surg, 1984; 38(2):124–127.

Gundry, "Modification of Myocardial Ischemic in Normal and Hypertrophied Hearts Utilizing Diastolic Retroperfusion of the Coronary Veins," *J Thorac Cardiovasc Surg*, 1982; 83:659–669.

Haendchen et al., "Prevention of Ischemic Injury and Early Reperfusion Derangements by Hypothermic Retroperfusion," *J Am Coll Cardiol*, 1983; 1(4):1067–1080.

Hammond et al., "Retrograde Coronary Sinus Perfusion: A Method of Myocardial Protection in the Dog During Left Coronary Artery Occlusion," Ann Surg, 1967; 166(1):139–147.

Kalmbach et al., "Cardioplegia Delivery by Combined Aortic Root and Coronary Sinus Perfusion," *Ann Thorac Surg*, 1989; 47:316–317.

Kar and Nordlander, "Coronary Veins: An Alternate Route to Ischemic Myocardium," *Heart and Lung*, Mar. 1992, vol. 21, No. 2, pp. 148–155.

Leggett et al., "Fiberoptic Cardioscopy Under Cardiopulmonary Bypass: Potential for Cardioscopy Surgery?" *Ann Thorac Surg*, 1994;58:222–225.

Lust et al., "Improved Protection of Chronically Inflow–limited Myocardium with Retrograde Coronary Sinus Cardioplegia," *Circulation III*, 1988;78(5):217–223.

Markov et al., "Reversal of Acute Myocardial Ischemia in Closed Chest Animals by Retrograde Perfusion of the Coronary Sinus with Arterial Blood," *Acta Cardiologica*, 1976; XXXI(3):185–199.

Medex, Inc., MX220 Single Tuohy–Borst Adaptor: Instructions for Use, 1992.

Medi–Tech, Boston Scientific Corporation, "Occlusion Balloon Catheters: Instruction for Use," Rev. Jun., 1991.

Medtronic Bio–Medicus, Inc., "Bio_Medicus Cannula Instructions for Use Manual, Sterile and Non–Pyrogenic Single–Use Only," PN 85281 Rev C(10–91).

Medtronic Bio–Medicus, Inc., "Bio_Medicus Cannula Introducer Instructions for Use Manual," PN 85146–Rev. C(7/91).

Medtronic Bio–Medicus Femoral Cannulae advertisement, ©1991.

Medtronic Bio–Medicus Pediatric Cannulae advertisement, ©1991.

Medtronic Bio–Medicus Percutaneous Cannula Kits advertisements, ©1991.

Meerbaum et al., "Diastolic Retroperfusion of Acutely Ischemic Myocardium," *Am J Cardiol*, 1976; 37:588–598.

Meerbaum et al., "Hypothermic Coronary Venous Phased Retroperfusion: A Closed–Chest Treatment of Acute Regional Myocardial Ischemia," *Circulation*, 1982; 65(7) 1435–1445.

Meerbaum et al., "Retrograde Lysis of Coronary Artery Thrombus by Coronary Venouse Strepokinase Administration," *J Am Coll Cardiol*, 1983; 1(5):1262–1267.

Menasche et al., "Cardioplegia by Way of the coronary Sinus for Valvular and Coronary Surgery," *JACC*, 1991; 18(2):628–636.

Menasche et al., "Retrograde Cardioplegia through the Coronary Sinus," *Ann Thorac Surg*, 1987; 44:214–216.

Menasche et al., "Retrograde Warm Blood Cardioplegia Preserves Hypertrophied Myocardium: A Clinical Study," *Ann Thorac Surg*, 1994; 57:1429–1435.

Ogawa, K. "Aortic Arch Reconstruction Without Aortic Cross–Clamping Using Separate Extracorporeal Circulation," *J Jpn Assn Thorac Surg*, 1993; pp. 2185–2190.

Okita et al., "Utilization of Triple–Lumen Balloon Catheter for Occlusion of the Ascending Aorta During Distal Aortic Arch Surgery with Hypothermic Retrograde Cerebral Circulation Technique Through Left Thoracotomy," *Journal of Cardiac Surgery*, 1996; 10:699–702.

Peters, W. S., "The Promise of Cardioscopic Surgery," *AustralAs J Cardiac Thorac Surg*, 1993; 2(3):152–154.

Pilling Surgical Instruments, Vascular Clamps—Cooley Brochure, p. 385 (no date).

Razi, D..M., "The Challenge of Calcific Aortitis," J Cardiac Surg, 1993; 8:102–107.

Research Medical, Inc., Cardioplegia Products, Product Catalog 1995.

Research Medical, Inc., Fem Flex Femoral Percutaneous Cannulae, advertisement, *Ann Thorac Surg*, Jan., 1995, p. A38.

Research Medical, Inc. Product Catalog 1995, Cardioplegia Products.

Ropchan et al., "Salvage of Ischemic Myocardium by Nonsynchronized Retroperfusion in the Pig," *The Journal of Thoracic and Cardiovascular Surgery*, Sep. 1992, vol. 104, No. 3, pp. 619–625.

Sabiston, D.C., Textbook of Surgery, $10^{th}$ Ed., 1972, pp. 2021–2023, 2114–2121.

Sakaguchi et al "Aortic Valve Replacement and Coronary Artery Bypass," *J Jpn Assoc for Thoracic Surg*, 1993;41(6):1063–1068.

Shumway, "Forward Versus Retrograde Coronary Perfusion for Direct Vision Surgery of Acquired Aortic Valvular Disease," *J Thoracic and Cardiovasc Surg*, 1959; 75–80.

Takahashi, M., "Retrograde Coronary Sinus Perfusion for Myocardial protection in Aortic A valve Surgery," *J Jpn Assn Thorac Surg*, 1982;30(3):306–318.

Uchida et al, "Percutaneou Cardiomyotomy ad Valvulotomy with Angioscopic Guidance," *American Heart Journal*, 1991;121(4, part I):1221–1224.

Uchida et al., "Percutaneous Fiberoptic Angioscopy of the Cardiac Valves," *Am Heart J*, 1991;121(6, part I):1791–1798.

Yamaguchi, A., "A Case of Reoperation Using a Balloon Catheter with Blocked Pars Ascendes Aortae," *Kyobu Geka*, 1991; 42(11):961–964.

Andersen et al., "Transluminal Implantation of Artificial Heart Valves . . . ," *European Heart Journal*, 1992;13:704–708.

Baxter Healthcare Corporation, "Fogarty Occlusion Catheter: Instructions for Use," ©1994.

Buckberg, "Strategies and Logic of Cardioplegic Delivery to Prevent, Avoid, and Reverse Ischemic and Reperfusion Damage," *J Thorac Cardio Vasc Surg*, 1987;93:127–129.

Cosgrove, "Management of the Calcified Aorta: An alternative method of occlusion," *Ann Thorac Surg*, 1983;36:718–719.

Crooke et al, "Biventricular Distribution of Cold Blood Cardioplegic Solution Administered b Different Retrograde Techniques," *J Cardiac Thorac Surg*, 1991;102(4):631–636.

Datascope FDA 510 (k) Application, "Percluder–DL Occluding Balloon," Oct. 12, 1993.

DLP, Inc., Directions for Use: Cardioplegic Pressure Cannula with Vent Line, Code #14009 9 Gauge (no date).

DLP Medtronic Alternative Access Cannulae Brochure, ©1995.

Erath et al., "Balloon Catheter Occlusion of the Ascending Aorta," *Ann Thorac Surg*, 1983;35:560–561.

Foster et al., "Proximal Control of Aorta with a Balloon Catheter," *Surg, Gynecology & Obstetrics*, 1971; pp. 693–694.

Gundry et al., "A Comparison of Retrograde of Cardioplegia Versus Antegrade Cardioplegia in the Presence of Coronary Artery Obstruction," *Ann Thorac Surg*, 1984;38(2):124–127.

Leggett et al., "Fiberoptic Cardioscopy Under Cardiopulmonary Bypass: Potential for Cardioscopic Surgery?" *Ann Thorac Surg* 1994;58:222–225.

Lust et al., "Improved Protection of Chronically Inflow–limited Myocardium with Retrograde Coronary Sinus Cardioplegia," *Circulation III*, 1988:78(5):217–223.

Medex, Inc., MX220 Single Tuohy–Borst Adaptor: Instructions for Use, 1992.

Medi–Tech, Boston Scientific Corporation, "Occlusion Balloon Catheters: Instructions for Use,", Rev. Jun., 1991.

Medtronic Bio–Medicus Femoral Cannulae advertisement, ©1991.

Medtronic Bio–Medicus Percutaneous Cannula Kits advertisement, ©1991.

Medtronic Bio–Medicus Pediatric Cannulae advertisement, ©1991.

Medtronic Bio–Medicus, Inc., "Bio–Medicus Cannula Instructions for Use Manual, Sterile and Non–Pyrogenic Single–Use Only" PN 85281 Rev C (10–91).

Medtronic Bio–Medicus, Inc., "Bio–Medicus Cannula Introducer Instructions for Use Manual," PN 85146–Rev. C (7/91).

Ogawa, "Aortic Arch Reconstruction without Aortic Cross––clamping Using Separate Extracorporeal Circulation," *J Jpn Assn Thorac Surg*, 1993; pp. 2185–2190.

Okita et al., "Utilization of Triple–lumen Balloon Catheter for Occlusion of the Ascending Aorta During Distal Aortic Arch Surgery with Hypothermic Retrograde Cerebral Circulation Technique Through Left Thoracotomy," *Journal of Cardiac Surgery*, 1996;10:699–702.

Peters, "The Promise of Cardioscopic Surgery," *AustalAs J Cardiac Thorac Surg*, 1993;2(3)152–154.

Pilling Surgical Instruments, Vascular Clamps—Cooley brochure, p. 385 (no date).

Razi, "The Challenge of Calcific Aortitis," *J Cardiac Thorac Surg*, 1993;8:102–107.

Research Medical, Inc., Cardioplegia Products, Product Catalog 1995.

Research Medical, Inc., Fem–Flex II Femoral Percutaneous Cannulae advertisement, *Ann Thorac Surg*, Jan., 1995, p. A38.

Rossi, "Long–term Cardiopulmonary Bypass by Peripheral Cannulation in a Model of Total Heart Failure," *J Thorac Cardio Vasc Surg*, 1990;100:914–921.

Sabiston, *Textbook of Surgery*, $10^{th}$ Ed. 1972, pp. 2021–2023,2114–2121.

Sakaguchi et al., "Aortic Valve Replacement and Coronary Artery Bypass," *J Jpn Assn for Thorac Surg*, 1993;41(6):1063–1068.

Takahashi, Retrograde Coronary Sinus Perfusion for Myocardial Protection in Aortic Valve Surgery,: *J Jpn Assn Thorac Surg*, 1982;30(3):306–318.

Uchida et al., "Percutaneous Cardiomyotomy and Valvulotomy with Angioscopoic Guidance," *Am Heart J*, 1991;121(4 part 1):1221–1224.

Uchida et al., "Percutaneous Fiberoptic Angioscopy of the Cardiac Valves," *Am Heart J*, 1991;121(6, part 1):1791–1798.

Yamaguchi, "A Case of Reoperation Using a Balloon Catheter with Blocked Pars Ascendes Aortae," *Kyobu Geka*, 1991;42(11):961–964.

\* cited by examiner

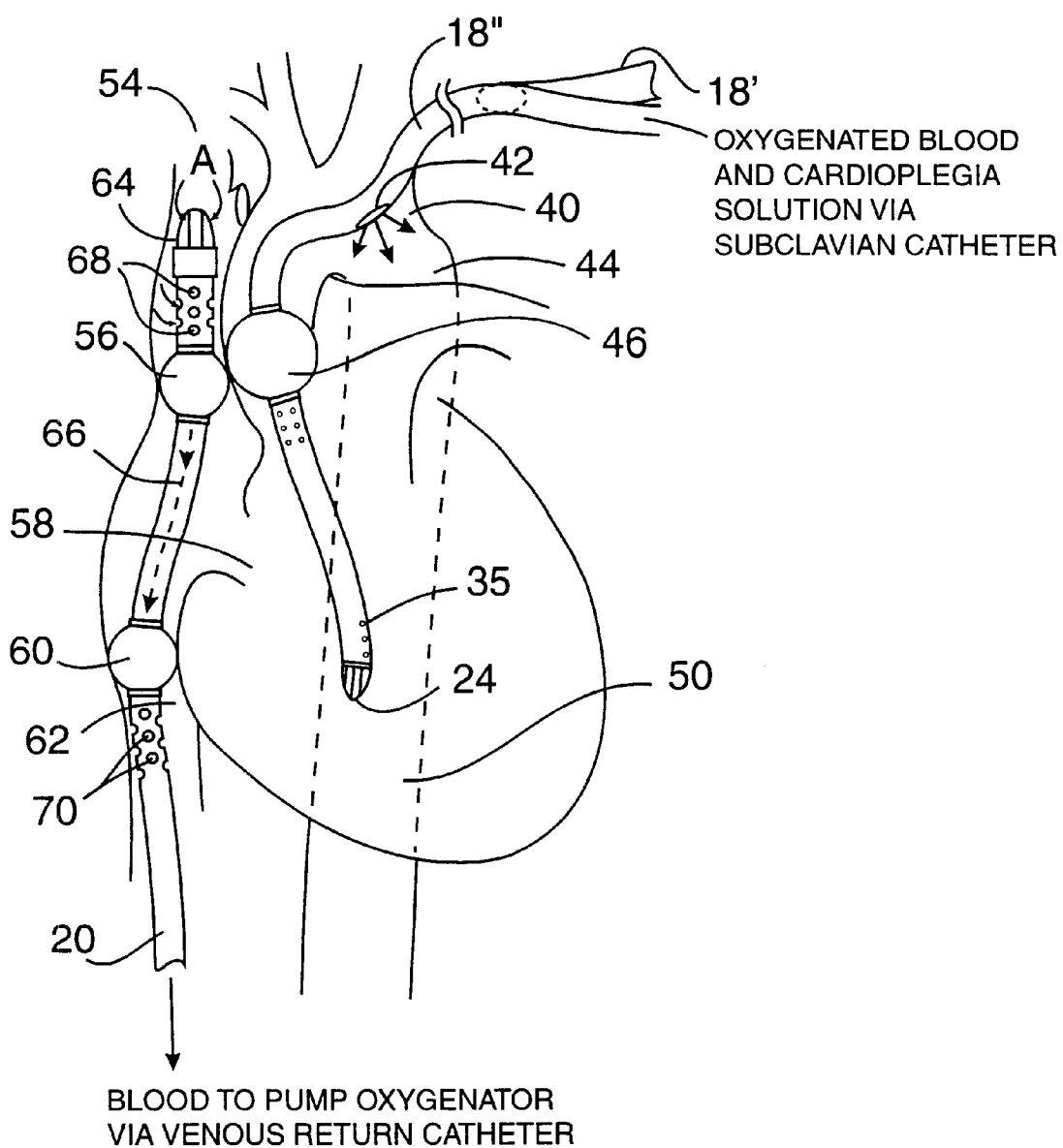

METHOD OF OCCLUDING A PATIENT'S ASCENDING AORTA AND DELIVERY CARDIOPLEGIC FLUID

CROSS-REFERENCE TO RELATED APPLICATION

This application is a continuation of U.S. patent application Ser. No. 08/566,405, filed Dec. 1, 1995, now issued as U.S. Pat. No. 5,765,568, which is a continuation-in-part of U.S. patent application Ser. No. 08/250,721, filed May 27, 1994, now issued as U.S. Pat. No. 5,478,309, the complete disclosures of which are incorporated herein by reference for all purposes.

BACKGROUND OF THE INVENTION

1. Field of the Invention

This invention relates generally to an extracorporeal circulation support system coupled to the blood circulation, and more particularly to an extracorporeal circulation support apparatus which directly vents the left ventricle.

2. Background of the Invention

Each year extracorporeal circulation support permits over 500,000 patients worldwide with disabling heart disease to undergo therapeutic cardiac operations. The primary goals of extracorporeal circulation support for heart surgery are, (i) to provide life-support functions, (ii) a motionless decompressed heart, (iii) a dry bloodless field of view for the surgeon, and (iv) adequate myocardial protection.

One method of extracorporeal support includes a basic heart-lung life-support system. Oxygen-poor blood is diverted from the venous circulation of the patient and transported to the heartlung machine where reoxygenation occurs, carbon dioxide is discarded and heat regulation, warming or cooling, is accomplished. This processed blood is then perfused into the patient's arterial circulation for distribution throughout the entire body to nourish and maintain viability of the vital organs. Although current venous diversion and arterial perfusion methods can be combined with other measures to effectively isolate the heart for cardiac surgery, they are associated with disadvantages and limitations which contribute significantly to patient morbidity, mortality, and health care costs. Another method may involve using a left ventricle assist system to channel blood from the left ventricle into aortic circulation.

In order to perform coronary artery bypass, valve operations and other complex delicate surgical procedures on the heart, it is desirable to establish a resting, non-beating, non-distended state. This condition, along with a dry bloodless field, is ideal for safe manipulation and suturing of cardiac structures. It also contributes to decreased metabolic cardiac energy demands while promoting preservation of cellular functions. This non-beating state is accomplished by delivery of various methods including but not limited to delivery of a cardioplegia solution to the coronary circulation.

There are several methods of controlling distension, decompression or venting, and improved visibility of the heart during heart surgery. These include but are not limited to, (i) insertion of a catheter via the left atrium or a pulmonary vein that is directed across the mitral valve so that its openings at the top are positioned within the left ventricular chamber for venting of blood, (ii) inserting a catheter directly into the apex, of the left ventricular muscle with its openings at the tip positioned within the left ventricular chamber for venting of blood, (iii) placement of a catheter in the isolated segment of the ascending aorta for antegrade cardioplegia delivery that can be alternatively switched to a suction source to accomplish aortic root venting (decompression) but not left ventricular decompression (venting), and (iv) inserting a catheter across the aortic valve into the left ventricle to remove blood from the left ventricle and return it back into the arterial circulations These methods have several disadvantages including but not limited to requiring major sternotomy or thoracotomy.

Major invasive chest incisions are often associated with a higher incidence of morbidity including, but not limited to, intraoperative and post-operative bleeding, resulting in the likelihood of increased blood transfusion requirements, returns to surgery for re-exploration to control hemorrhage, longer healing and recovery times, pulmonary complications (such as lung collapse and pneumonia), catastrophic wound infection (mediastinitis), extensive scarring and adhesions, mechanical wound instability and disruption (dehiscence), chronic incisional pain, peripheral nerve and musculoskeletal dysfunction syndromes.

Developing a system with features that avoids surgical maneuvers, instrumentation and devices known to be associated with increased morbidity and mortality, while maintaining the conditions necessary to perform various cardiac interventions, is desirable. Such improvements have the likelihood of resulting in a favorable impact on patient care, quality of life, and health care costs.

Although peripherally inserted catheters of the prior art avoid direct cardiac trauma and can be placed without a major invasive chest incision (sternotomy or thoracotomy), they do not establish the condition of total extracorporeal circulation support.

It is thus desirable to develop an extracorporeal circulation support system coupled to the blood circulation which directly removes blood from the left ventricle. It is farther desirable to provide a method for directly venting the left ventricle.

SUMMARY OF THE INVENTION

Accordingly, an object of the present invention is to provide an extacorporeal circulation support system that occludes the aorta and directly vents the left ventricle.

Another object of the present invention is to provide an extracorporeal circulation support system with a vent lumen that directly vents the left ventricle.

A further object of the present invention is to provide an extracorporeal circulation support system coupled to the blood circulation and directly vents the left ventricle.

Still another object of the present invention is to provide a method for directly venting the left ventricle.

These and other objects of the invention are provided in an extracorporeal support system coupled to the blood circulation. An extacorporeal support apparatus and an arterial circulation support catheter are provided. The arterial circulation support catheter includes a blood lumen with a proximal end coupled to the extracorporeal support apparatus and a distal end inserted into the blood circulation. A vent lumen has a distal end that crosses the aortic valve into the left ventricle and provides direct venting of the left ventricle through the vent lumen. An arterial circulation support catheter occluding member is positioned in an interior or an exterior of the arterial circulation support catheter. A venous circulation support catheter includes a blood lumen with a proximal end coupled to the extracorporeal support apparatus and a distal end inserted into the blood circulation. A venous circulation support catheter occluding member is included and positioned in an interior or at an exterior of the venous circulation support catheter. The venous circulation support catheter occluding member occludes the superior vena cava and the inferior vena cava.

In another embodiment a method for venting the left ventricle of the heart is disclosed. An extracorporeal circulation support system is provided and includes an extracorporeal support apparatus, a venous circulation support catheter, an arterial circulation support catheter and a vent lumen. The arterial circulation support catheter and venous circulation support catheter are introduced into the blood circulation. A vent lumen distal end is positioned in the left ventricle, and the left ventricle is directly vented through the vent lumen.

An arterial circulation support catheter occluding member lumen can be coupled to the arterial circulation support catheter occluding member and positioned in the arterial circulation support catheter. The arterial circulation support occluding member can be slideably positioned in the blood lumen or in the arterial circulatory support occluding member lumen. The arterial circulation support catheter occluding member can be one or more clamps or balloons.

A venous circulation support catheter occluding member lumen can be coupled to the venous circulation support catheter occluding member and positioned in the venous circulation support catheter. The venous circulation support catheter occluding member can be slideably positioned in the venous circulation support catheter blood lumen or in the venous circulation support catheter occluding member lumen.

The arterial circulation support catheter may include an infusion lumen with a distal end that introduces an infusion medium into the aortic root. The infusion lumen may be positioned in the interior of the arterial circulation support catheter at the exterior of the arterial circulation support catheter, in the blood lumens adjacent to the blood lumen or in the arterial circulation support catheter adjacent to the blood lumen.

The venous circulation support catheter may also include an infusion lumen that introduces an infusion medium into the venous circulation. The infusion lumen can be positioned in the interior of the venous circulation support catheter, at the exterior of the venous circulation support catheter, in the blood lumen or in the venous circulation support catheter adjacent to the blood lumen. Inclusion of the infusion lumen permits the introduction of an infusion medium into the venous circulation and may also vent mediums from the venous circulation and/or the right heart either simultaneously or at alternate times.

An interventional lumen, for the introduction of a diagnostic or therapeutic device into the blood circulation, may be positioned in an interior or exterior of the arterial circulation support catheter or in the blood lumen.

BRIEF DESCRIPTION OF THE FIGURES

FIG. 3 is a schematic drawing illustrating positioning of the arterial and venous circulation support catheters of the present invention to achieve extracorporeal circulation support.

DETAILED DESCRIPTION

Figure 1:
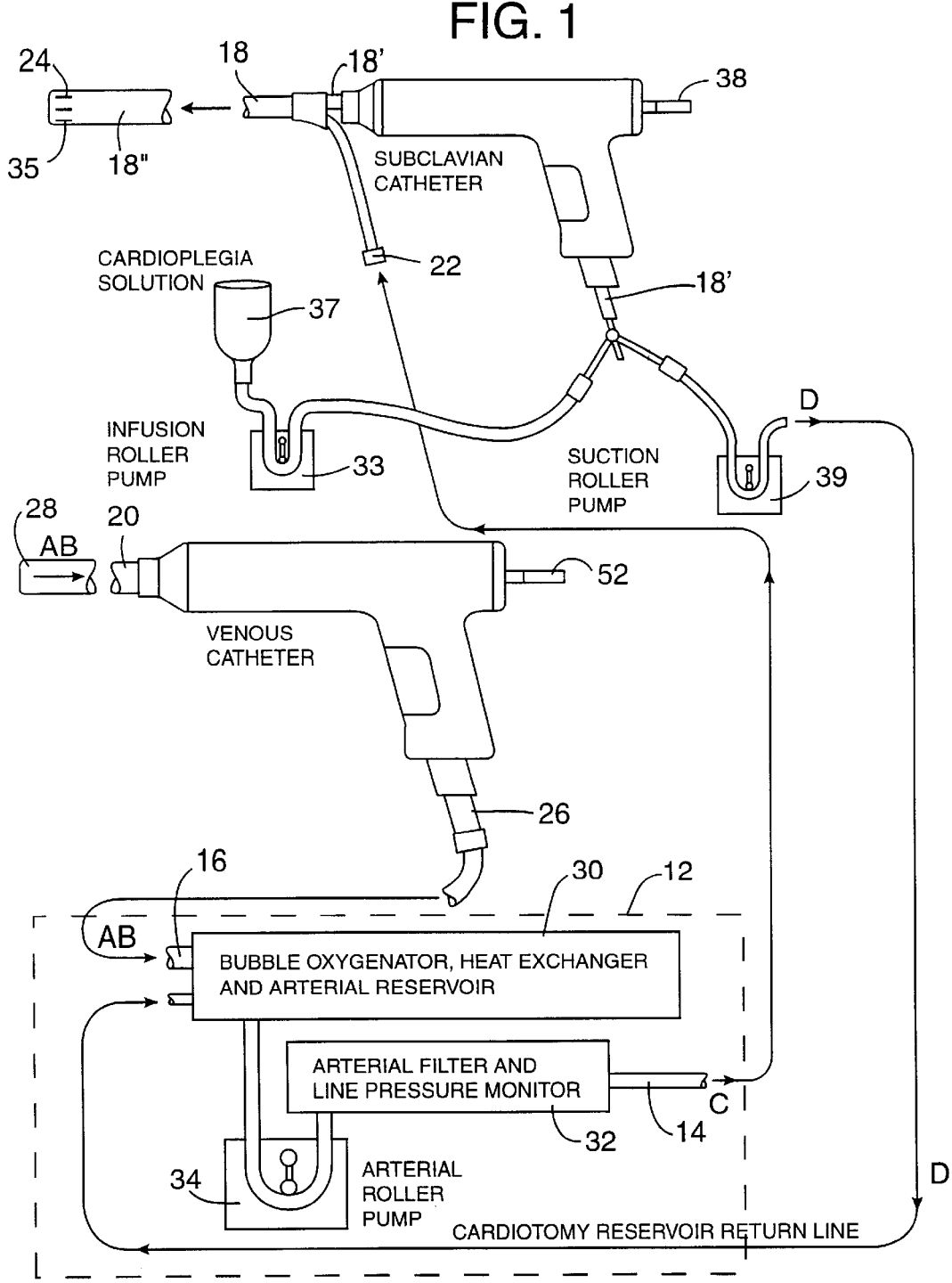
FIG. 1 is a schematic drawing illustrating the extracorporeal circulation support system of the present invention used for venting the left ventricle.

For purposes of this specification, venting is a method for decompressing or unloading a specific compartment of the circulation system. Typically, venting is the decompression of blood from a heart chamber. The left side of the heart is where oxygenated blood is introduced into the arterial system. The right side of the heart is where deoxygenated blood is introduced into the pulmonary system. The patient may be a human, an animal or a simulator.

Extracorporeal support system of the present invention can be used for a variety of procedures, both in the field of cardiology, as well as elsewhere in a patient. Cardiology applications (with a beating or non-beating heart) include but are not limited to, (i) CABG, (ii) congenital defects of the heart, (iii) valve repair and replacement, (iv) valvoplasty, (v) coronary bypass, (vi) heart venting, (vii) heart isolation and (viii) other procedures that are facilitated with heart venting without blood flowing into the heart chambers. The extracorporeal support system of the present invention is used with primary and reoperative surgical procedures, as well as a life support system.

An extracorporeal support system, denoted as 10, is inserted in the blood circulation. An extracorporeal support apparatus 12 provides for the delivery of re-oxygenated blood to the blood circulation and in one embodiment includes an outlet port 14 for the delivery of re-oxygenated blood to the arterial circulation, and an inlet port 16 for receiving blood from the venous circulation.

Extracorporeal support apparatus 12 can be a heart-lung apparatus, left ventricular assist device, roller pump, centrifugal device and the like. An arterial circulation support catheter 18 and a venous circulation support catheter 20 are provided. In one embodiment, arterial circulation support catheter 18 comprises a first flexible cannula 18' and a second flexible cannula 18". A proximal end 22 of arterial circulation support catheter 18 can be coupled to outlet port 14, and a distal end 24 is introduced into the blood circulation including but not limited to the arterial circulation. distal end 24 extends proximally to at least an occluding member coupled to arterial circulatory support catheter 18. A proximal end 26 of venous circulation support catheter 20 may be coupled to inlet port 16, and a distal end 28 is introduced into the blood circulation, including but not limited to the venous circulation.

Extracorporeal support apparatus 12 provides oxygenation and heating or cooling for blood and in one embodiment includes a bubble oxygenator 30, which incorporates a heat exchanger and an arterial reservoir, an arterial filter and line pressure monitor 32, and a pump 34 from which oxygenated blood is returned to arterial circulation as shown by arrow C. A method to stop or start the heart may include a fibrillation and defibrillation apparatus coupled to the heart.

First flexible cannula 18' may be selectively placed in communication with a pump 33. This pump may also provide for the delivery of a cardioactive agent 37 to the aortic root through one or more orifices 35 contained in distal end 24, or for venting blood from the aortic root. Vented blood need not be returned to extracorporeal support apparatus 12. In one method, the path of returned blood is shown by arrow D through a cardiotomy reservoir return line to bubble oxygenator 30 and a heat exchanger. The vented blood is thereafter oxygenated and then delivered to a pump 34 where it is returned into arterial circulation as shown by arrow C. In another method the path of blood extracted from the left ventricle is reintroduced into the arterial system distal to an arterial circulation support catheter occluding member.

In one embodiment, arterial circulation support catheter 18 may be minimally invasively inserted directly into the aorta. This technique may require inserting a thorascope through an intercostal incision. The descending thoracic aorta and distal arch are identified. The thorascope is further utilized to obtain an actual image of the cardiac anatomic structure.

Specifically and without limiting the scope of the present invention, the technique described in the preceding paragraph is used to assist the surgeon in fashioning a pair of circular tourniquet purse string sutures at the sight selected for insertion of the catheter into the descending thoracic aorta After the purse string sutures are fashioned, a side-biting vascular clamp is then applied to occlude and isolate the insertion site from the rest of the aorta. This maneuver prevents bleeding when the catheter is advanced through a hole made in the center of the purse strings. After the catheter is advanced through the hole, the tourniquets are drawn taunt to snugly seal the aortic tissue around the catheter entry site. The side-biting vascular clamp is then removed.

In another method to create the arteriotomy, a device is used which can facilitate the introduction and closure of the arteriotomy.

Arterial circulation support catheter 20 allows distal end 24 to transverse the aortic valve where distal end 24 has one or more openings for venting the left ventricle. Extracorporeal circulation support can be achieved with venous circulation support catheter 20 remotely inserted into the veins. Preferably, the insertion is in the femoral vein. Venous circulation support catheter 20 is then advanced and positioned at the atrio-caval junction by ultrasound or fluoroscopic techniques. To achieve delivery of blood into arterial circulation, one or more arterial catheters may be inserted peripherally into arterial vessels and then advanced and positioned in the aorta, or directly inserted into the aorta by utilizing purse string sutures and the like.

Figure 2:
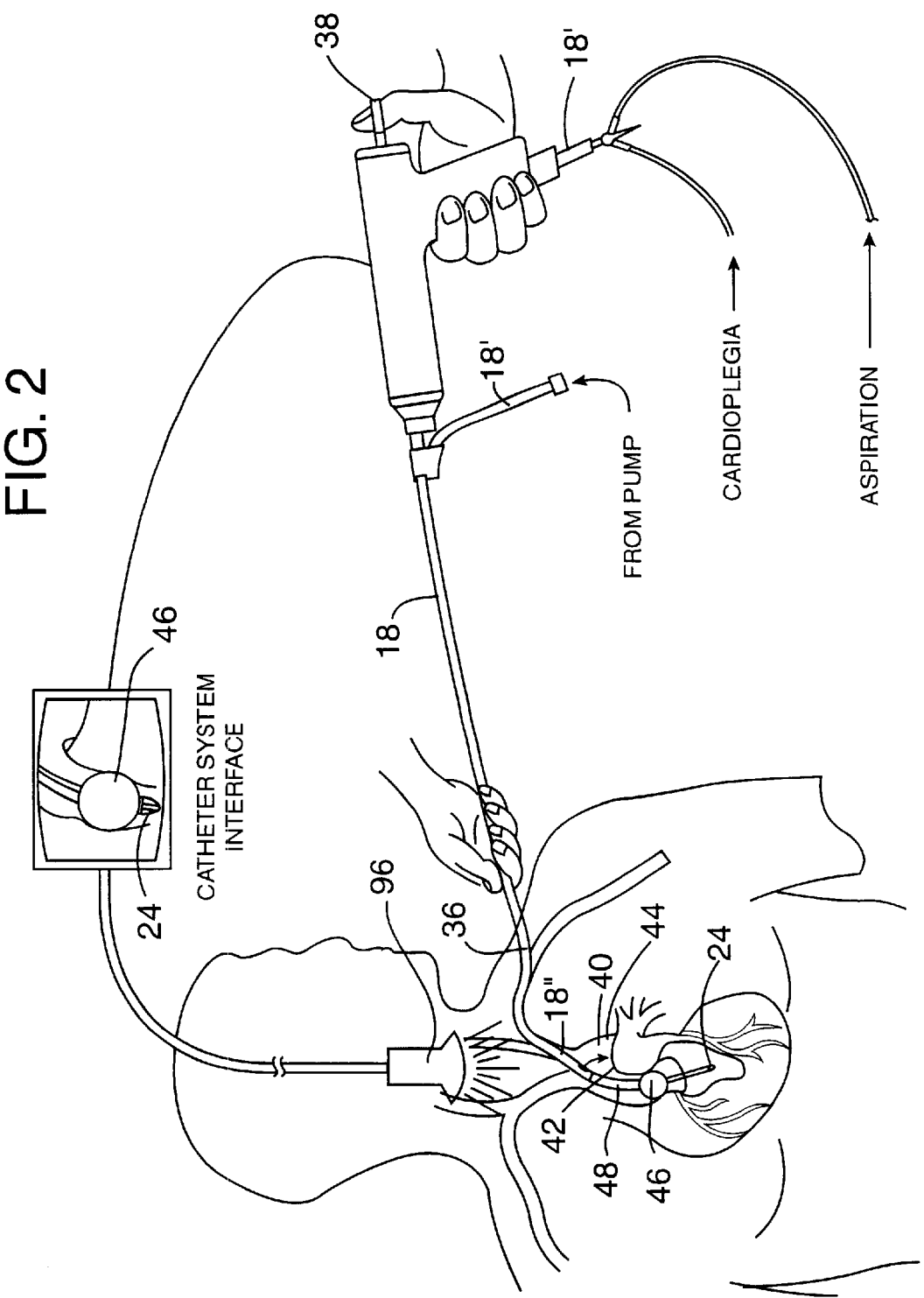
FIG. 2 is a schematic drawing of an arterial circulation support catheter inserted into the subclavian artery.
Figure 4A:
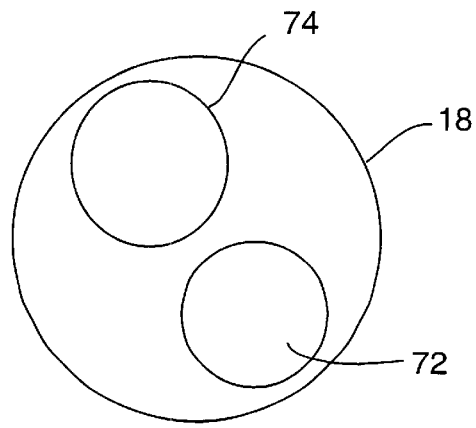
FIGS. 4(a) through 4(d) are cross-sectional views of different arterial a circulation support catheters of the present invention
Figure 4C:
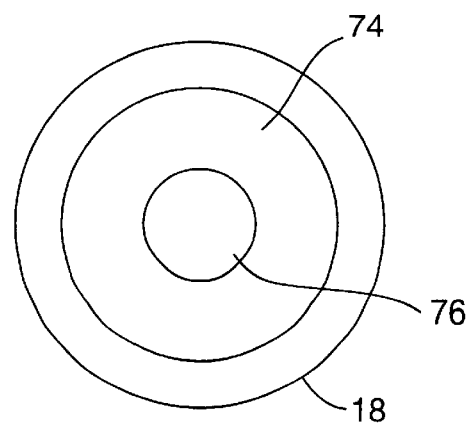
Figure 4B:
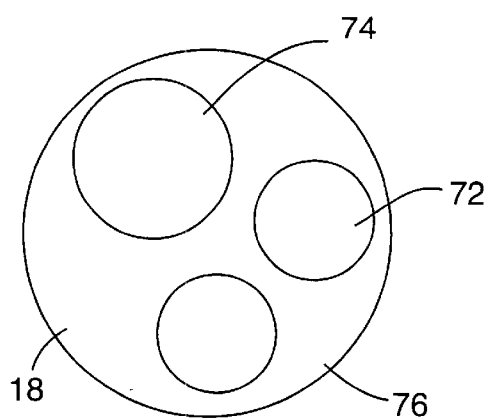
Figure 4D:
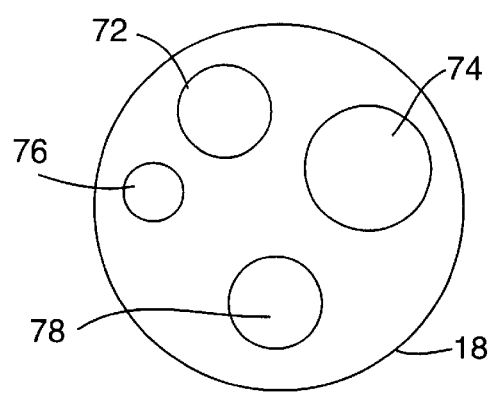

As illustrated in FIG. 2, arterial circulation support catheter 18 is inserted in subclavian artery 36. Arterial circulation support catheter 18 and venous circulatory support catheter 20 may be manipulated with a joy stick, steerable and non-steerable guide wires, and the like. In one embodiment arterial circulation support catheter 18 is steered by a joy stick 38 into aortic arch 40 such that a first opening 42 of arterial circulation support catheter 18 is positioned adjacent to the descending or thoracic aorta 44. This permits the flow of oxygenated blood from extacorporeal support apparatus 12 into the arterial circulation. First flexible cannula 18' is slideably extendable from second flexible cannula 18" and has one or more occluding members 46, which can be clamps, balloons, and the like, positioned in an interior or exterior of arterial circulation support catheter 18 adjacent to distal end 24. For purposes of this specification, and without limitation, occluding member 46 shall hereafter be referred to as balloon 46. In one embodiment, distal end 24 is spaced a sufficient fixed distance from balloon 46 to transverse aortic valve 48. In another embodiment, distal end 24 is positioned directly adjacent to balloon 46. Because of the slidable relationship of first and second flexible cannulas 18' and 18" the distance between balloon 46 and a second balloon ( if included) can be varied. This slidable relationship permits arterial circulation support catheter 18 to be used with a greater spectrum of patients.

In a further embodiment, distal end 24 is extendable distally relative to balloon 46 to permit distal end 24 to be advanced across aortic valve 48 and into left ventricle 50. Balloon 46 may be positioned in the ascending aorta by utilizing ultrasound or fluoroscopic imagery. One or more apertures can be formed in distal end 24 to introduce a variety of different cardioactive agents.

Referring now to FIG. 3, venous circulation support catheter 20 is inserted peripherally into the femoral vein and advanced with the use of a joy stick, guide wire and the like. In one embodiment, to assist the surgeon in locating distal end 24, and also to position balloon 46 in the aortic arch, a sensor is fixed adjacent to distal end 24. The sensor can be made of an ultrasonic reflective material, coated with a piezoelectric or other material, or may be a radiopaque marker for fluoroscopically imaging distal end 24. One or more sensors are fixed to second flexible cannula 18" adjacent to proximal and distal ends of balloon 46 respectively.

Venous circulation support catheter 20 is then positioned by ultrasound, Doppler, electromagnetic mark, fluoroscopy, and the like such that distal end 28 extends into superior vena cava 54 Superior vena cava 54 is occluded by a first occluding member 56 which is located adjacent to distal end 28 and placed cephalad to atrio-caval junction 58. An optional second occluding member 60 is coupled to venous circulation support catheter 20 and spaced proximally from first occluding member 56 either in a fixed or adjustable relationship. First and second occluding members 56 and 60 can be balloons, clamps, deployment devices including but not limited to umbrellas and the like, positioned both at the interior and exterior of venous circulation support catheter 20, and the like.

For purposes of this specification, and without limitation, occluding members 46, 56 and 60 will hereafter be called a balloon. Suitable balloon materials include but are not limited to, silicon rubber, polyurethane, latex nylon, polyamide, polyethylene and the like. First and second flexible cannulas 18' and 18" may be made of silicon rubber, polyvinyl chloride, polyurethane, ethylene, nylon and the like. Inflation of balloons 56 and 60, as well as balloon 46 may be achieved through the injection of a saline solution or other biocompatible fluid by a syringe through lumens contained within the respective catheters 18 and 20. Instead of a fluid, a gas including but not limited to $CO_2$ may be used.

Second balloon 60 is positioned proximately of atrio-caval junction 58 to occlude inferior vena cava 62. First and second balloons 56 and 60 straddle atrio-caval junction 58 and when inflated isolate the heart from blood flow into the right atrium of the heart. Arrows A illustrate the blood flow from superior vena cava 54 through one or more venous orifices 64 which are located in distal end 28 of venous circulation support catheter 20. Venous orifice 64 communicates with the axially extending blood lumen 66 and provide a flow path to extracorporeal support apparatus 12.

Extracorporeal circulation support during heart surgery requires the insertion of venous circulation support catheter 20 through a peripheral vein access site and thereafter positioning distal venous return ports of catheter 20 in superior and inferior vena cava 54 and 62 at atrio-caval junction 58. Venous circulatory support catheter 20 contains one or more balloons 56 and/or 58 that allow the choice of either partial or total heart isolation. Total heart isolation occurs if balloon 56, and/or the combination of balloons 56 and 60, completely occluded both inferior and superior vena cava 62 and 54, thereby preventing blood flow into the right atrium.

An insertion site for venous circulation support catheter 20 may be the femoral vein, iliac vein, subclavian vein, axillary vein, or internal jugular vein. Insertion of venous circulation support catheter 20 through a peripheral vein access site avoids, (i) the necessity for a major chest incision to expose the heart, and (ii) eliminates the surgical trauma that would occur to the right atrium, superior vena cava 54, and inferior vena cava 62. This procedure eliminates costly surgical instruments, sutures, tourniquets, and reduces the operative time associated with conventional approaches to extracorporeal circulation support.

To provide blood in arterial circulation, arterial circulation support catheter 18 is inserted peripherally into arterial vessels to permit first flexible cannula 18' to be advanced through the vessel into the ascending aorta. In one embodiment, arterial circulation support catheter 18 carries balloon 46 proximately of distal end 24 for occluding the aorta after balloon 46 is positioned in the ascending aorta cephalad of the junction of the coronary arteries in the aortic root. Arterial circulation support catheter 18 is then connected to extracorporeal support apparatus 12 which is then activated to permit oxygenated blood to be delivered to arterial circulation. Cardioactive agents may be infused into the aortic root to arrest the heart. Additionally, contrast agents may also be introduced to visualize coronary structures. Balloons 56 and 60 of venous circulation support catheter 20 are expanded sufficiently to preclude blood flow from inferior and superior vena cava 62 and 54 into the right atrium. Total extracorporeal circulation support is achieved. If the vena cava is not totally occluded by complete inflation of one or both of balloons 56 and 60 the result is partial isolation of the heart.

In one embodiment, a pair of venous sensors are carried by venous circulation support catheter 20 and located at the distal and proximal ends of first balloon 56. These sensors may be made of a material that is reflective of ultrasound or coated with a piezoelectric or other material. The piezoelectric material may generate an electric signal for transmission to a catheter system interface. The transmission is then presented on a monitor to assist the surgeon in visualizing the distal and proximal ends of first balloon 56 during its passage through the femoral vein and ultimate positioning in atrio-caval junction 58. Alternatively, the sensors may be radiopaque markers for use in fluoroscopically imaging the location of balloon 56 Other methods of imaging known in the at may also be used.

Inferior vena cava 62 is occluded by the inflation of second balloon 60. Blood flowing toward the right atrium after balloon 60 is inflated is precluded from flowing past balloon 60 and enters venous circulation support catheter 20 through venous return ports 68. The blood is then transported directly to extracorporeal support apparatus 12.

Arterial circulation support catheter 18 may include one or more different lumens which may provide for the introduction and expulsion of blood to and from the arterial circulation.

As illustrated in FIGS. 4(a) to 4(d), a variety lumens can be included and positioned in an interior or at an exterior of arterial circulation support catheter. These lumens can include, (i) a vent lumen 72, (ii) a blood lumen 74, (iii) an infusion lumen 76, and an intervention lumen 78. Vent lumen 72 is used to directly vent blood from left ventricle 50, introduce fluids or other devices. An inflation lumen coupled to balloon 46 may also be included.

Vent lumen 72 has a distal end that crosses the aortic valve into left ventricle 50. Vent lumen 72 may also be utilized as an infusion lumen and/or introduce devices. Arterial circulation support catheter 18 can be a blood lumen, or alternatively include a separate blood lumen 74 which can be positioned adjacent to vent lumen 72, infusion lumen 76 or intervention lumen 78.

Infusion lumen 76 and intervention lumen 78 can be positioned in blood as lumen 74. Infusion lumen 76 can introduce a variety of different infusion mediums into the arterial circulation. Suitable infusion mediums include but are not limited to, a cardio-active agent, one or more contrast agents, an iontropic agent, and the like. Infusion lumen 76 may introduce the infusion medium into the aortic root and also be used to vent from the aortic root either simultaneously or at alternate times. Intervention lumen 78 introduces a variety of different diagnostic or therapeutic devices into the arterial circulation.

Figure 5A:
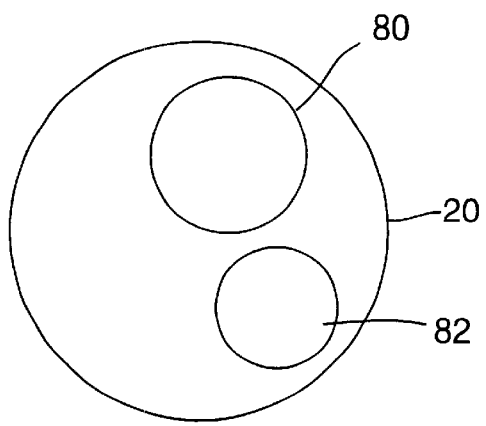
FIGS. 5(a) through 5(c) are cross-sectional views of different venous circulation support catheters of the present invention.
Figure 5B:
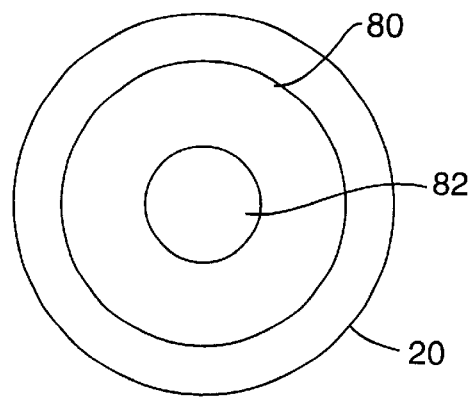
Figure 5C:
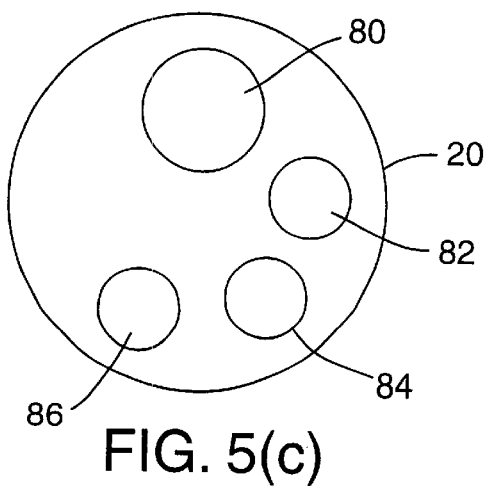

Referring now to FIGS. 5(a) through 5(c), venous circulation support catheter 20 can include a blood lumen 80, an infusion lumen 82, an intervention lumen 84 and a vent lumen 86. The functions of blood lumen 80, infusion lumen 82, intervention lumen 84 and vent lumen 86 are substantially the same as their equivalent lumens associated with arterial circulation support catheter 18. Each of the lumens can be positioned in an interior or at an exterior of venous lumen 20. Venous circulation support catheter 20 can be a blood lumen. Alternatively, a separate blood lumen 80 can be positioned in an interior of venous circulation support catheter 20. Infusion lumen 82 introduces an infusion median into the venous circulation, and can be positioned adjacent to or in blood lumen 80. Intervention lumen 84 may also be positioned adjacent to or in blood lumen 80. Additionally, an inflation lumen can be coupled to balloon 56 and/or 60.

Figure 6:
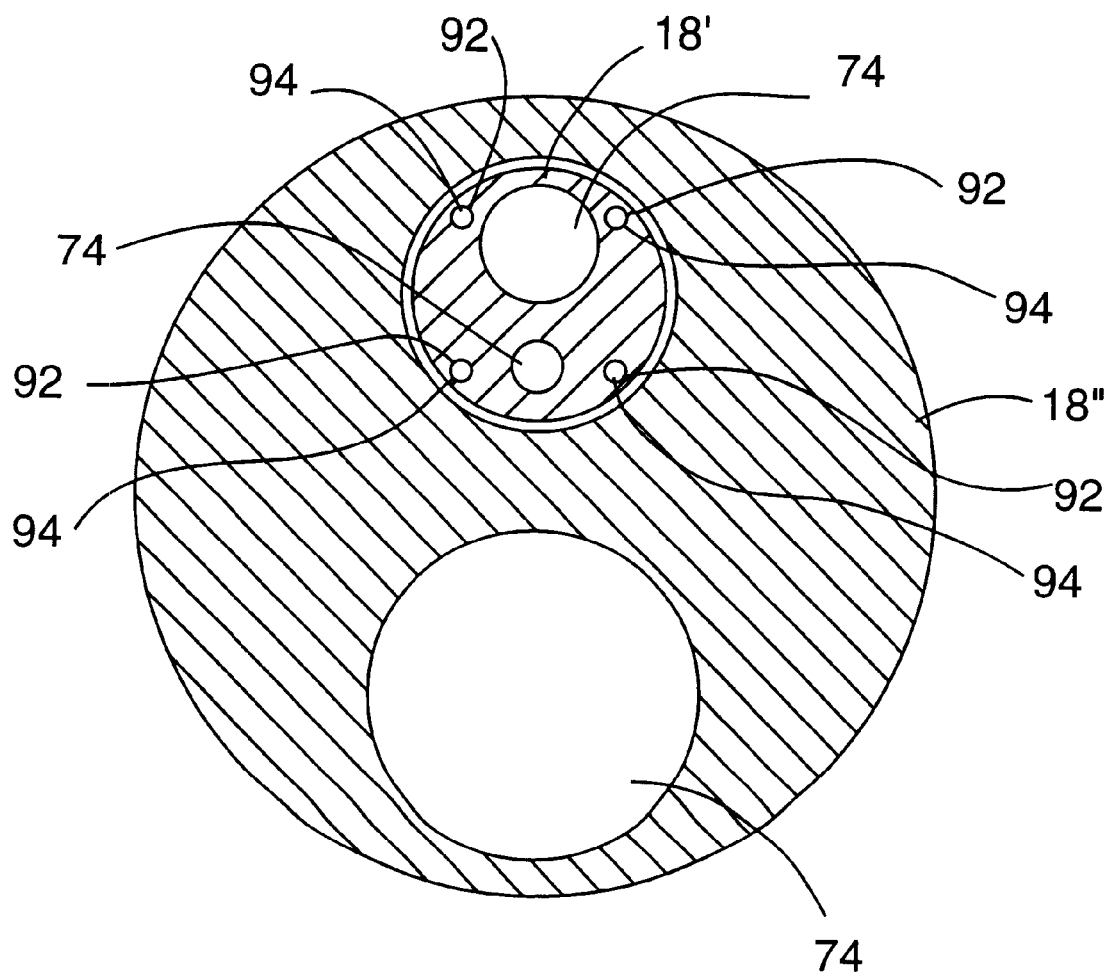
FIG. 6 is a cross-sectional view of an arterial circulation support catheter.

By reference now to FIG. 6, it can be seen that first flexible cannula 18' may have four steering lumens 92 which extend in part axially through flexible cannula 18' to permit steering wires 94 to pass through first flexible cannula 18' in slidable relationship where the distal ends of the steering wires 94 are connected to the distal end of the first flexible cannula 18'. Through the manipulation of joy stick 38 appropriate linkage permits steering wires 94 to be placed in tension relative to each other. This permits distal end 24 of arterial circulation support catheter 18 to articulate.

A clearance exists between first flexible cannula 18' and second flexible cannula 18" to permit flexible cannula 18' to be advanced through second flexible cannula 18". Movement in either direction can induce the slidable advancement of first cannula 18' within second cannula 18". This arrangement permits the surgeon to position first opening 42 of second flexible cannula 18" in aortic arch 40 and thereafter to slide first cannula 18' relative to second cannula 18" and position occluding member 46 in the aortic root. In one embodiment a first sensor is carried by first flexible cannula 18' proximally of balloon 46 and a second sensor is positioned at the distal end of balloon 46 where the sensors may be made of material that efficiently reflects ultrasonic waves.

Ultrasound waves are detectable by a device such as a transesophageal echo device 96 (FIG. 2) for a clear presentation of the extremities of balloon 46. This provides a more precise positioning of balloon 46 in aortic arch 40 cephalid of the junction of the coronary arteries. Fluoroscopic imaging, Doppler, electromagnetic positioning, and other methods may also be used to positioned the catheters.

Other embodiments of arterial circulation support catheter 18 may utilize a reflective material to promote fluoroscopic imaging of balloon 46 extremities to achieve proper positioning in the aortic root. Suitable reflective materials include barium sulfate, bismuth subcarbonate and the like. First and second flexible cannulas 18' and 18" may also be in part, (i) impregnated with materials for positioning and visualization, including but not limited to radiopaque materials such as barium sulfate, bismuth subcarboxiate or iodine containing molecules, (ii) impregnated with tungsten, (iii) include materials to enhance performance characteristics including but not limited to fillers such as plasticizer or other pigmentation or anti-oxidants, or (iv) coated with blood physiology agents, and other agents and materials to promote visualization of arterial circulation support catheter 18 and balloon 46 within the arterial vessel and aortic wall.

Figure 7:
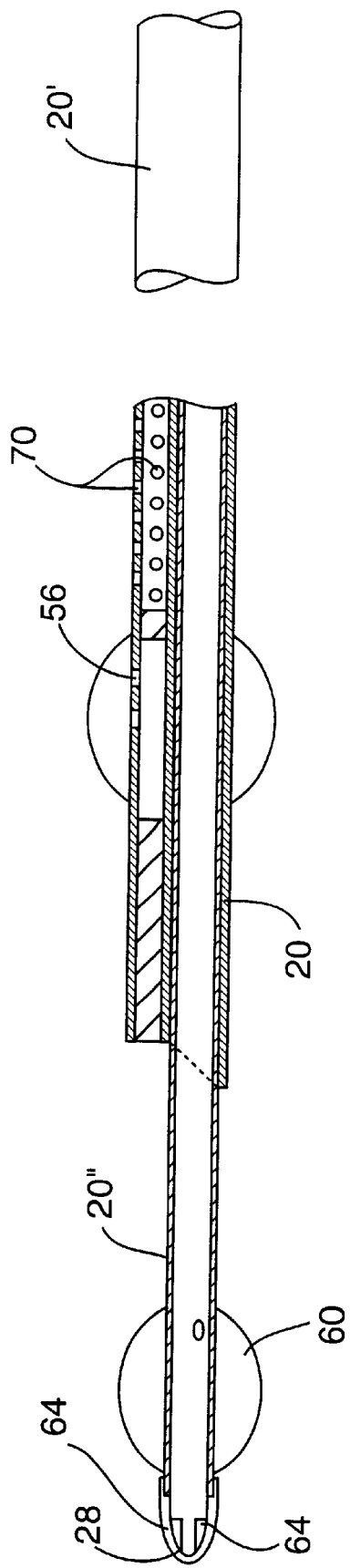
FIG. 7 is a cross-sectional view of a distal end of a venous circulation support catheter.

Another embodiment of venous catheter 20 is shown in FIG. 7 which permits the spacing between first and second balloons 56 and 60 to be adjustable. Only a single balloon need be used This enhances venous circulation support catheter's 20 universality of use.

In this embodiment, venous circulation support catheter 20 is comprised of a first flexible cannula 20' which is in part slideably contained for slidable axial movement relative to a second flexible cannula 20". Because of the slideable relationship of the first and second flexible cannulas 20' and 20" the distance between first balloon 56 and second balloon 60 can be varied. This slideable relationship permits venous circulation support catheter 20 to be used with a greater spectrum of patients.

Venous circulation support catheter 20 has one or more orifices 64 located in distal end 28 which redirect blood flowing through superior vena cava 54 toward the right atrium where the blood is transported through venous circulation support catheter 20 to extracorporeal support apparatus 12. Blood flowing through inferior vena cava 62 is prevented from reaching the right atrium by the inflation of second balloon 60. Blood flows through second venous return posts 70 into venous circulation support catheter 20 where the blood is transported to extracorporeal support apparatus 12. Distal end 28 of venous circulation support catheter 20 may have an associated distal sensor. The distal sensor may be coated with a piezoelectric material, made of a suitable ultrasound reflective material, or be a radiopaque marker for fluoroscopically imaging the location of distal end 28 of venous circulation support catheter 20. Additionally, one or more steering wires may be included to provide articulation and promote passage of venous circulation support catheter 20 through the venous circulation.

Venous circulation support catheter 20 may include one or more different cavities or lumens which provide for the introduction and expulsion of blood to and from the venous circulation.

Figure 8:
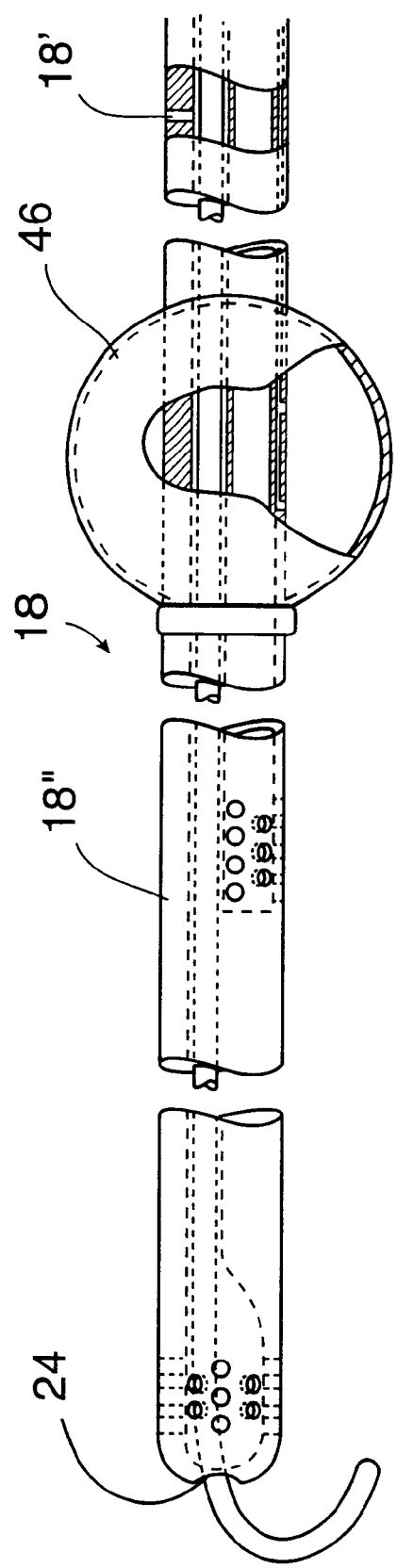
FIG. 8 is a phantom and part cross-sectional view of an embodiment of an arterial circulation support catheter of the present invention.
Figure 10:
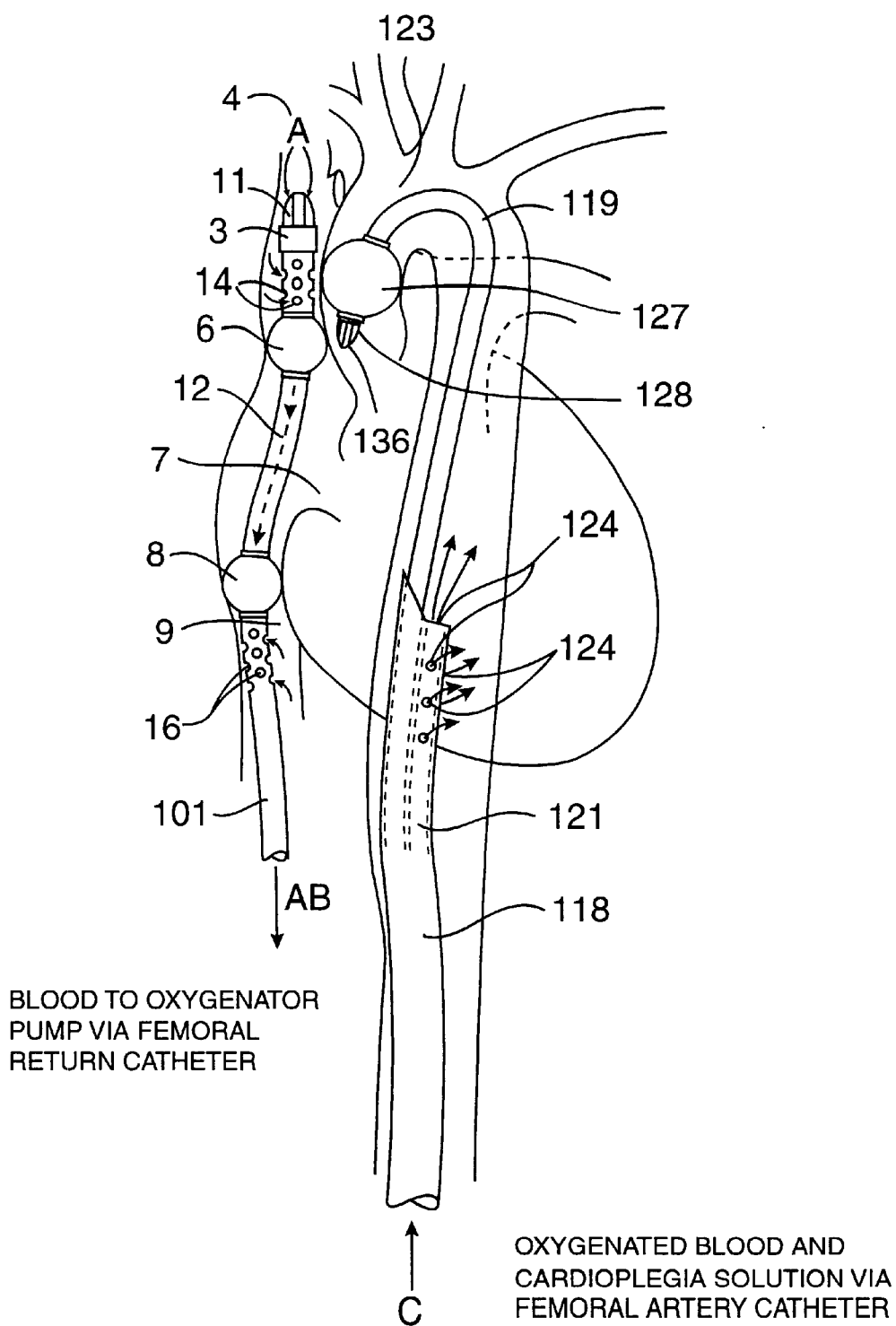
FIG. 10 is a schematic view illustrating an arterial circulation support catheter inserted through the femoral artery and a venous circulation support catheter occluding the superior and inferior vena cava.

An embodiment illustrating total isolation of the heart is shown in FIG. 10, described later on in this specification. Although not shown in the figures, isolation of the heart may be achieved by utilizing two venous circulation support catheters 20 of substantially identical construction. These catheters each have an inflatable balloon 60 at their distal ends 28. One of the catheters 20 is inserted through a peripheral vein, the jugular vein for example, distal end 28 is advanced into superior vena cava 54 and positioned to occlude superior vena cave 54 at atrio-caval junction 58. Orifices located proximally of balloon 60 permit blood flowing toward the right atrium to be diverted into a lumen within venous circulation support catheter 20 for transport to extracorporeal support apparatus 12. Similarly, second venous circulation support catheter 20 is inserted through the femoral vein and advanced and positioned in inferior vena cava 62 at atrio-caval junction 58. Balloon 60 is then inflated and blood flow redirected through one or more orifices located proximally of balloon 60 to extracorporeal support apparatus 12. Arterial circulation support catheter 18 of FIG. 8 provides an extended distal end 24 which may pass across aortic valve 48 and into left ventricle 50 to provide direct venting. A cardioactive agent 37 can be delivered into the aortic root, as in the above-described embodiments of arterial circulation support catheter 18, or the same flow path may be used for aspiration of the aortic root. Extended distal end 24 of arterial circulation support catheter 18 is positioned in aortic arch 40 after balloon 46 where first flexible cannula 18' is extendable from second flexible cannula 18". One or more flow lumens are included in first flexible cannula 18' to provide for blood venting from left ventricle 50 to extracorporeal support apparatus 12.

Figure 9:
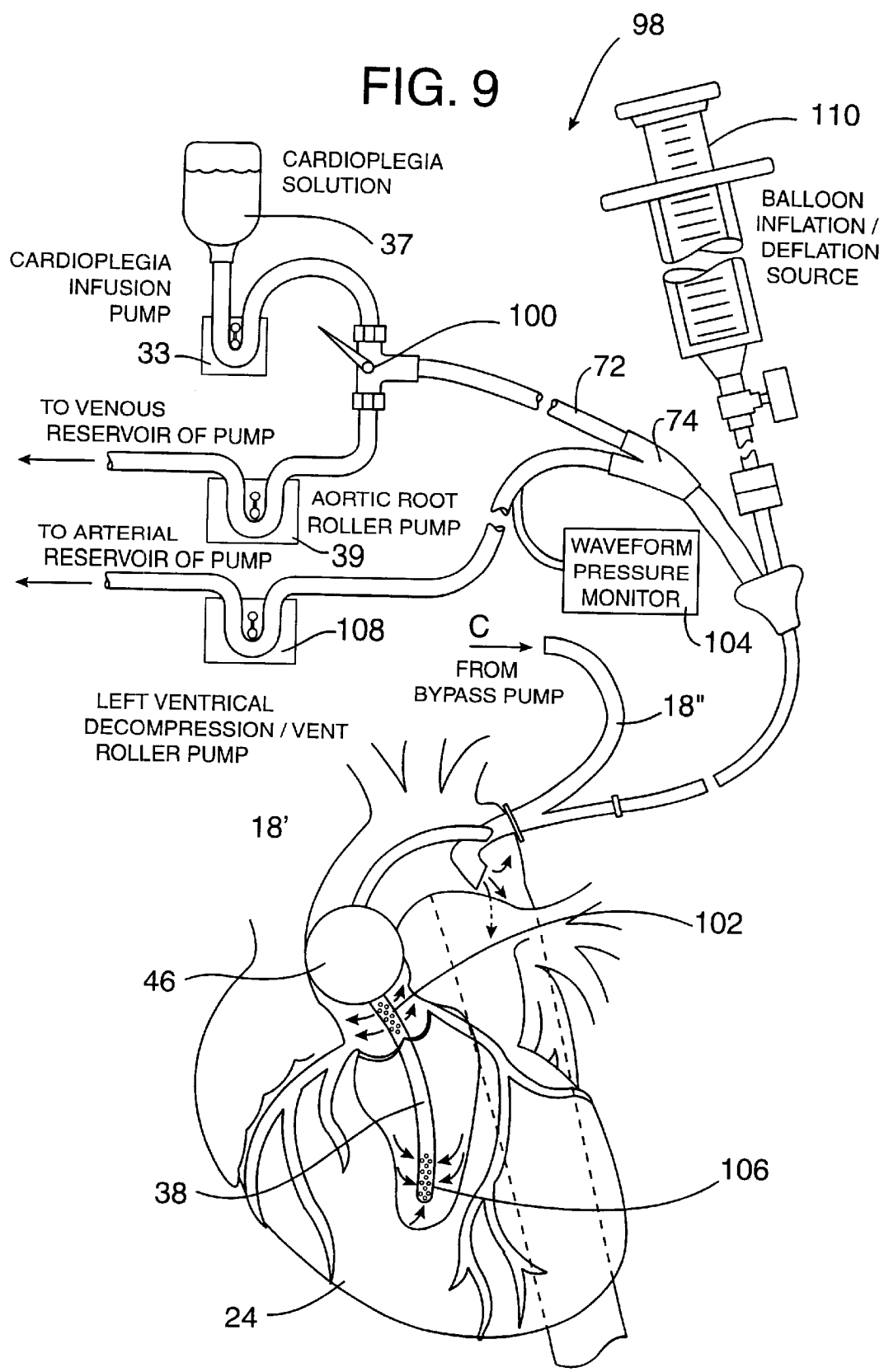
FIG. 9 is a schematic view illustrating an arterial circulation support catheter of the present invention inserted directly in the descending aorta.

A specific embodiment for venting using arterial circulation support catheter circuit 98 is illustrated in FIG. 9. These elements provide for injection of cardioactive agent 37, venting of the aortic root, balloon 46 inflation and deflation, arterial circulation of blood from the bypass pump, and left ventricle 50 decompression. Arterial circulation support catheter 18 may also be inserted into ascending aortic arch 40 after a sternotomy has been performed and the heart exposed.

Distal end 24 is positioned in left ventricle 50 where blood may be suctioned through one or more arterial venting orifices 106. Arterial circulation support catheter 18 allows blood in left ventricle 50 to be vented Simultaneously, blood present in the aortic root may also be vented through one or more venting orifices 102. Cardioactive agent 37 may thereafter be infused through venting orifice 102 through a vent lumen 72, and the solution will flow into the coronary arteries and stop the heart.

FIG. 10 illustrates an embodiment where total isolation of the heart is achieved. Arterial circulation support catheter 18 is advanced through the femoral artery and positioned such that balloon 46 may be inflated to occlude the aorta cephalad of the aortic root. Oxygenated blood is then delivered through blood lumen 74, or alternatively through vent lumen 72, into arterial circulation. Vent lumen 72, blood lumen 74 or infusion lumen 76 delivers cardioactive agent 37 to arrest the heart, provide venting the aortic root, and provide extension of distal end 24 into left ventricle 50 across the aortic valve. This permits decompression of left ventricle 50 before the right atrium is isolated by inflation of balloon 56 and/or balloons 56 and 60.

Another method for providing extracorporeal circulation support during heart surgery includes using two arterial circulation support catheters 18. Both are advanced into aortic arch 40. Venous circulation support catheter 20 is then positioned to preclude blood flow into the right atrium. Passage of blood from the aortic root into the systemic arterial circulation is occluded. Cardioactive agent 37 is then infused into the aortic root to arrest the heart and the aortic root is then vented. The right atrium and the heart are isolated. Total heart isolation is achieved.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

What is claimed is:

1. A method of placing a patient on cardiopulmonary bypass comprising:

introducing a catheter into a subclavian artery, the catheter including a shaft having a first lumen communicating with a first opening and a second lumen communicating with a second opening, and an expandable member attached to the shaft distal to the first opening and proximal to the second opening and being movable between a collapsed shape and an expanded shape;

endovascularly advancing the catheter from the subclavian artery to position the expandable member in the ascending aorta;

moving the expandable member into the expanded shape to occlude the ascending aorta;

infusing oxygenated blood into the arterial system downstream of the expandable member through the first lumen and the first opening; and arresting the heart.

2. The method of claim 1 wherein the step of arresting the heart comprises delivering cardioplegic fluid upstream of the expandable member through the second lumen and the second opening.

3. The method of claim 1 further comprising removing blood from a vein of the patient through a venous cannula, oxygenating the withdrawn blood, and delivering the oxygenated blood to the arterial system through the first lumen and first opening of the catheter.

4. The method of claim 3 further comprising occluding at least one of the vena cava during the step of removing blood.

* * * * *